(12) United States Patent
Spangenberg et al.

(10) Patent No.: US 10,605,717 B2
(45) Date of Patent: Mar. 31, 2020

(54) APPARATUS FOR ANALYZING URINE

(71) Applicant: DURAVIT AKTIENGESELLSCHAFT, Hornberg (DE)

(72) Inventors: Bernd Spangenberg, Offenburg (DE); Dirk Jansen, Ohlsbach (DE); Bernd Kaiser, Endingen (DE)

(73) Assignee: DURAVIT AKTIENGESELLSCHAFT, Hornberg (DE)

( * ) Notice: Subject to any disclaimer, the term of this patent is extended or adjusted under 35 U.S.C. 154(b) by 18 days.

(21) Appl. No.: 15/518,132

(22) PCT Filed: Oct. 5, 2015

(86) PCT No.: PCT/EP2015/072908
§ 371 (c)(1),
(2) Date: Apr. 10, 2017

(87) PCT Pub. No.: WO2016/066372
PCT Pub. Date: May 6, 2016

(65) Prior Publication Data
US 2017/0284925 A1   Oct. 5, 2017

(30) Foreign Application Priority Data
Oct. 31, 2014   (DE) .......................... 10 2014 115 914

(51) Int. Cl.
*G01N 33/493* (2006.01)
*A61B 5/20* (2006.01)
(Continued)

(52) U.S. Cl.
CPC ......... *G01N 15/1459* (2013.01); *A61B 5/208* (2013.01); *A61B 10/007* (2013.01);
(Continued)

(58) Field of Classification Search
USPC ........................................................ 422/82
See application file for complete search history.

(56) References Cited

U.S. PATENT DOCUMENTS 3,568,215 A * 3/1971 Riedel ..................... B63B 29/00
4/317
4,943,416 A * 7/1990 Kikuchi ........... G01N 35/00029
422/63
(Continued)

FOREIGN PATENT DOCUMENTS

DE   102010061035 A1   6/2012
WO   2006065705 A2    6/2006

*Primary Examiner* — Jill A Warden
*Assistant Examiner* — Brittany I Fisher
(74) *Attorney, Agent, or Firm* — Lucas & Mercanti, LLP

(57) ABSTRACT

An apparatus for analyzing urine, including: a feeding and discharging device that delivers a quantity of urine into an analysis chamber of a urine test strip and discharges a quantity of urine from an analysis chamber of a urine test strip, the analysis chamber having an analysis zone. The feeding and discharging device includes a movably mounted feeding and/or discharging element for delivering a quantity of urine into a delivery zone in the analysis chamber and/or discharging a quantity of urine from a discharge zone in the analysis chamber. A detection device detects an at least sectoral variation of an optically detectable parameter, which varies in an optically detectable manner in accordance with the composition of a quantity of urine that contacts the analysis zone and produces detection data describing at least one optically detected parameter in the analysis zone or a variation of such a parameter.

21 Claims, 8 Drawing Sheets

(51) Int. Cl.
*G01N 15/14* (2006.01)
*A61B 10/00* (2006.01)
G01N 21/47 (2006.01)
E03D 11/02 (2006.01)

(52) U.S. Cl.
CPC ........... *G01N 15/14* (2013.01); *G01N 33/493* (2013.01); *E03D 11/02* (2013.01); *G01N 2015/1486* (2013.01); *G01N 2021/4707* (2013.01)

(56) References Cited

U.S. PATENT DOCUMENTS

| | | | | |
|---|---|---|---|---|
| 4,961,431 | A | * 10/1990 | Ikenaga | A61B 5/14507 600/573 |
| 5,087,556 | A | 2/1992 | Ertinghausen | |
| 5,111,539 | A | * 5/1992 | Hiruta | A61B 5/02241 4/301 |
| 5,271,895 | A | 12/1993 | McCroskey et al. | |
| 5,846,490 | A | 12/1998 | Yokota et al. | |
| 6,221,678 | B1 | * 4/2001 | Chandler | G01N 33/54366 422/423 |
| 2004/0146428 | A1 | * 7/2004 | Minter | A61B 10/007 422/412 |
| 2008/0286879 | A1 | * 11/2008 | Lee | G01N 33/558 436/164 |
| 2009/0324448 | A1 | * 12/2009 | Yano | G01N 1/4077 422/82.05 |
| 2012/0329170 | A1 | 12/2012 | Matsumoto | |

* cited by examiner

APPARATUS FOR ANALYZING URINE

The present application is a 371 of International application PCT/EP2015/072908, filed Oct. 5, 2015, which claims priority of DE 10 2014 115 914.4, filed Oct. 31, 2014, the priority of these applications is hereby claimed and these applications are incorporated herein by reference.

BACKGROUND OF THE INVENTION

The invention pertains to an apparatus device for analyzing urine, to a urine test strip device, and to a sanitary facility comprising such an apparatus.

Apparatuses for analyzing urine and possibly other endogenous fluids are known and serve in general to analyze a certain quantity of urine with respect to its chemical composition and/or the percentages of its constituents. Urine test strips, with which a certain quantity of urine comes in contact, are usually used for this purpose. The evaluation or observation of a change in an optically detectable parameter, i.e., especially a color change, of an analysis zone of the urine test strip makes it possible to draw conclusions concerning the chemical composition of the urine and/or the percentages of its constituents.

So far the conventional approach has been manually to wet urine test strips of the type in question with a certain quantity of urine, which can be done by, for example, dipping a urine test strip into a sample container. The urine-wetted test strips are then examined in a spectrometer. This represents a comparatively complicated procedure for realizing a urinalysis and thus is deserving of improvement.

SUMMARY OF THE INVENTION

The invention is therefore based on the goal of providing an apparatus for analyzing urine which is superior to what has been used in the past.

The goal is achieved according to the invention by an apparatus for analyzing urine, which apparatus comprises at least:
  a feed and discharge device, which is set up to deliver a certain quantity of urine to an analysis chamber of a urine test strip comprising at least one analysis zone and for discharging a certain quantity of urine from an analysis chamber of a urine test strip comprising at least one analysis zone, wherein the feed and discharge device comprises at least one movably supported feed and/or discharge element for delivering a certain quantity of urine to a delivery zone of the analysis chamber of the urine test strip and/or for discharging a certain quantity of urine from a discharge zone of the analysis chamber of the urine test strip; and
  a detection device, which is set up to detect, at least in a certain area, a change in an at least one optically detectable parameter of the analysis zone or of a corresponding zone of the urine test strip or of a corresponding test strip, which parameter changes detectably as a function of the composition of a quantity of urine coming in contact with it, and to generate detection data which describe at least one optically detectable parameter of the analysis zone or of a corresponding zone or which describe a change in such a parameter.

The apparatus according to the invention for analyzing urine, referred to in the following in brief as the "apparatus", comprises as its essential components, therefore, a feed and discharge device and a detection device. Obviously, the apparatus can also comprise several feed and discharge devices and/or several detection devices.

The feed and discharge device serves to deliver a certain quantity of urine to at least one urine test strip analysis chamber comprising an analysis zone and to discharge a certain quantity of urine from a urine test strip analysis chamber comprising an analysis zone. Correspondingly, the feed and discharge device comprises at least one movably supported feed and/or discharge element for delivering a certain quantity of urine to a delivery zone of the urine test strip analysis chamber and for discharging a certain quantity of urine from a discharge zone of the urine test strip analysis chamber. The feed and discharge device and/or the at least one feed and/or discharge element belonging to this device therefore makes it possible to deliver and/or to discharge a certain quantity of urine—in general a certain quantity of fluid—to a corresponding delivery zone or from a corresponding discharge zone and thus to and/or from a urine test strip analysis chamber, in which a corresponding analysis zone is present.

Although, in principle, the certain quantity of urine could be delivered and discharged by means of only a single feed and discharge element, which serves both to deliver a certain quantity of urine to a corresponding delivery zone and also to carry away a certain quantity of urine from a corresponding discharge zone, the feed and discharge device typically comprises at least one separate feed element for delivering a certain quantity of urine to a corresponding delivery zone and at least one separate discharge element for carrying away a certain quantity of urine from a corresponding discharge zone.

The movable support of a corresponding feed and/or discharge element makes it possible to control the movement of the element in question toward the corresponding urine test strip delivery and discharge zones and away from corresponding urine test strip delivery and discharge zones. A corresponding feed and/or discharge element can typically be moved between two end points. What defines a first end point is that, at this point, a certain quantity of urine can be delivered to a corresponding urine test strip delivery zone or a certain quantity of urine can be discharged from a corresponding urine test strip discharge zone. The second end point is defined correspondingly in that, at this end point, a certain quantity of urine cannot be delivered to a corresponding urine test strip delivery zone or discharged from a corresponding urine test strip discharge zone.

The movement of a corresponding feed and/or discharge element typically proceeds along a defined axis or path of movement, which can be linear and translational, for example. Other axes or paths of movement such as an arc-shaped path are also conceivable in principle.

Insofar as several feed and/or discharge elements are provided, these can be moved along similarly shaped or nonsimilarly shaped axes or paths of movement. The movement of the feed and/or discharge elements can proceed simultaneously or offset in time. It is advisable, however, for the several feed and/or discharge elements to move simultaneously along parallel axes or paths of movement.

The detection device serves to detect a change, at least in a certain area, in at least one optically detectable parameter of a corresponding analysis zone of a urine test strip. The optically detectable parameter changes in an optically detectable manner, i.e., for example, by undergoing a change in color and/or a change in the color intensity, as a function of the composition of a quantity of urine wetting or in contact with the analysis zone. Thus the color or the color intensity of the analysis zone is an appropriate optically detectable parameter. So that a corresponding change in the optically detectable parameter or in one such parameter can be detected, the detection device comprises suitably adapted detection means, especially optical means. Such detection means can be, for example, one or more optical scanners.

In addition to the detection of a change, at least in a certain area, of at least one optically detectable parameter of a corresponding urine test strip analysis zone, the detection device also serves to generate a set of detection data. The detection data generated by the detection device describe at least one optically detectable or detected parameter of the analysis zone or describe a change in such a parameter. Therefore, the detection data can describe, for example, a color, a color intensity, or a color change of the analysis zone.

Because the detection device advisably is set up to communicate with at least one evaluation device, which is set up to evaluate the detection data generated by the detection device and to acquire evaluation data describing an analysis of the quantity of urine present on the analysis zone of the urine test strip, the detection data can be transmitted to appropriate evaluation devices, in which, on the basis of the detection data, conclusions can be drawn concerning the chemical composition or the percentages of the constituents of the quantity of urine applied to the analysis zone. For this purpose, the apparatus preferably comprises a transmitting and/or receiving device assigned to the detection device, which transmitter and/or receiver makes possible the wired or wireless transmission of the corresponding detection data. The apparatus can therefore be connected to or integrated into a local or global data network such as into a local intranet or the Internet by means of Bluetooth or WiFi technology, for example.

The feed and discharge device as well as the detection device are typically operated by an apparatus-side control unit assigned to these devices. In the control unit, typically at least one control program is stored, according to which a 'concertized', i.e., coordinated, control of the operation of the feed and discharge device, of the detection device, and possibly of additional devices belonging to the apparatus according to the invention, is possible. The latter include in particular the following devices, which will explained in greater detail further below: pressure-determining devices, pump devices, and valve devices installed in a bypass line.

Various operating modes of the apparatus according to the invention can be realized by the control unit and/or the at least one control program stored in it. Appropriate operating modes provide in particular for the withdrawal of a certain quantity of urine; for the delivery of the certain quantity of urine or of the certain quantity of withdrawn urine to a urine test strip analysis chamber; for the discharge of the certain quantity of urine or of the certain quantity of withdrawn urine from a urine test strip analysis chamber; for procedures for flushing the feed and discharge device; for procedures for flushing the feed and discharge elements; for procedures for flushing certain sections of line leading to the feed and/or discharge elements, i.e., for flushing feed lines and discharge lines; and for procedures for flushing a urine test strip, i.e., in particular for flushing a urine test strip analysis chamber, etc.

Corresponding operating modes of the apparatus according to the invention can be activatable or deactivatable, i.e., activated or deactivated, in various ways. The activation or deactivation can be accomplished by means of, for example, mobile terminal devices, which are to be understood as cell phones, smartphones, laptops, tablets, etc., which can communicate with a transmitting and/or receiving device in the apparatus over a communications connection. It can also be possible to control operations by voice commands, wherein the apparatus in this case is equipped with a suitably adapted voice recognition device. Corresponding operating modes of the apparatus can also be activated or deactivated in fully automatic or partially automatic fashion, as is obvious.

Overall, the apparatus according to the invention makes it possible to perform a urinalysis in a simple and integrated manner and thus represents an improvement over the prior art described above.

The apparatus according to the invention can, as will be explained again further below, be assigned to or integrated into a sanitary facility comprising a flush toilet. Therefore, corresponding urinalyses as well as, in principle, analyses of other substances excreted from the body can be carried out in a practical manner at the site where the urine is excreted. To perform a urinalysis, therefore, it is no longer necessary, as has been conventional until now, to transfer the urine to an appropriate container, so that the urine test strip can be wetted appropriately. The urinalysis can thus be conducted within the sanitary facility accommodating the apparatus according to the invention or within one such facility.

To realize the movements of corresponding feed and/or discharge elements, the feed and discharge device advisably comprises at least one drive device connected to the at least one feed and/or discharge element. By means of the drive device, the at least one feed and/or discharge element can be moved toward the urine test strip delivery and/or discharge zone or one such zone in such a way that a tip, especially a cannula-like tip, of the feed and/or discharge element penetrates the urine test strip delivery and/or discharge zone to deliver and/or to discharge the quantity of urine or a quantity of urine to or from the urine test strip analysis chamber. For this purpose, the drive device comprises, for example, a motorized drive, i.e., for example, an electric motor, or is configured as such.

At this point it should be remarked generally that a corresponding feed and/or discharge element typically has a cannula-like or tubular shape. A corresponding feed and/or discharge element is thus typically configured as a hollow cylindrical body enclosing a passage through which a fluid can flow. The tip of the feed and/or discharge element can be constructed so that it tapers down to a point or a slant, so that it can easily penetrate or perforate an element, especially the encapsulating element to be explained in greater detail below, which covers a urine test strip-side delivery and/or discharge zone.

The apparatus advisably encompasses at least one conveying device, which is set up to convey at least one urine test strip into a defined detection zone on the apparatus side, in which the detection device can detect a change, at least in a certain area, in the at least one optically detectable parameter and/or to convey the test strip out of the detection zone or out of one such zone. By means of such a conveying device, one or several urine test strips can thus be effectively conveyed into or out of a corresponding detection zone of the detection device. The conveying device thus makes possible the conveyance of a single or of multiple corresponding urine test strips. The conveying device can be set up to convey corresponding urine test strips either continuously or discontinuously.

So that it can convey corresponding urine test strips, the conveying device can, for example, comprise at least one rotatably supported transport element with conveying sections for conveyance of at least one urine test strip or it can be configured as such a transport element. The transport element can be, for example, a pimple wheel with conveying sections configured with pimples arranged a certain distance apart around the circumference to convey at least one urine test strip. The pimples, typically projecting radially from the pimple wheel, thus define conveying sections by means of which urine test strips can be conveyed by the rotation of the pimple wheel. Alternatively or in addition, the conveying device can comprise at least one conveyor belt with conveying sections for conveying at least one urine test strip or can be configured as such a belt. Again, alternatively or in addition, the conveying device can comprise at least one transport roller, from which a set, to be explained in greater detail below, of several serially connected strip-like or belt-like urine test strips can be unrolled or onto which a set of several serially connected strip-like or belt-like urine test strip can be rolled up, or can be configured as such a roller. Each of the transport rollers can also be equipped with conveying sections for conveying at least one urine test strip. In particular, the conveying rollers can be corresponding pimple wheels.

The conveying device can in particular comprise at least two transport rollers, so that a set of several serially connected strip-like or belt-like urine test strips can be unrolled from the first transport roller in such a way that at least one urine test strip to be conveyed to the detection zone can be or is moved into the detection zone and can be rolled up onto a second transport roller in such a way that the at least one urine test strip can be moved or is moved out of the detection zone. This is an especially practical principle, according to which unused urine test strips are stored in the form of a corresponding set rolled up on a corresponding first transport roller and can be unrolled from it. Used urine test strips, i.e., in particular urine test strips which have been moved into the detection zone, contacted with urine by means of the feed and discharge device, and correspondingly "scanned" by the detection device, can be rolled up on the second transport roller and thus collected on it.

To determine whether a urine test strip has reached the detection zone and thus is located in the position required for the detection of a corresponding optically detectable parameter of a urine test strip analysis zone or for the detection of a change in such a parameter, the apparatus can comprise at least one position-determining device. Such a position-determining device is set up correspondingly to determine the correct positioning of a urine test strip, i.e., the position of the strip required for the detection of a corresponding optically detectable parameter of a urine test strip analyze zone or for the detection of a change in such a parameter by means of the detection device. The position-determining device can for this purpose comprise, for example, light barriers or be configured as such. The determination of the position of a urine test strip by a position-determining device can thus in general be carried out by optical means.

The apparatus can also comprise at least one separation device following the detection device to separate at least one urine test strip from a set of several serially connected strip-like or belt-like urine test strips. Therefore, a single or several appropriately used urine test strips can be separated from the set by such a separation device and thus handled individually, i.e., in particular disposed of. The separation device therefore serves in general to cut off used urine test strips from unused urine test strips and to separate them from the set in question. The separation device can for this purpose comprise a blade or a laser or be configured as such.

The apparatus advisably comprises at least one housing part, which is configured to hold the feed and discharge device, the detection device, and possibly additional devices of the apparatus to be cited in the following. The housing part thus makes it possible to accommodate the devices belonging to the apparatus in a comparatively compact manner.

At least one receiver section, which is configured to accept used urine test strips, i.e., in particular test strips which have in the meantime been treated with a certain quantity of urine, especially after the detection device has detected, at least in a certain area, the change in the at least one optically detectable parameter of the analysis zone of the urine test strip, can be detachably mountable or mounted on the housing part.

In addition, at least one support section for supporting at least one corresponding conveying device, especially in the form of a transport roller, can be configured on the housing part. From a structural point of view, the support section can be a bolt-like or pin-like projection, on which a corresponding conveying device, especially in the form of a transport roller, is rotatably supportable or supported. The bolt-like or pin-like projection typically forms the rotational axis of the conveying device, i.e., in particular of the transport roller.

Especially in conjunction with the flushing of the feed and discharge device mentioned above and generally in conjunction with various operating modes of the apparatus or of the sanitary facility comprising this apparatus, it can be advisable for at least one bypass line to be present, which connects a feed line leading to a feed element and a discharge line leading to a discharge element. At least one valve device for opening and closing the bypass line is advisably installed in the bypass line.

To convey urine through the apparatus, i.e., in particular to convey it into a corresponding urine test strip analysis chamber or to discharge it from a corresponding urine test strip analysis chamber, at least one pump device installed in a feed line leading to a feed element and/or at least one pump device installed in a discharge line leading from a discharge element is advisably present. The at least one pump device installed in a feed line leading to a feed element is set up to convey a certain quantity of urine into the or into a urine test strip delivery zone or into a corresponding urine test strip analysis chamber. The at least one pump device installed in a discharge line leading from a discharge element is set up to convey a certain quantity of urine from the or from a urine test strip discharge zone or from a corresponding urine test strip analysis chamber. The pump devices can comprise conventional pumps such as a centrifugal pumps or rotary piston pumps, etc., or be configured as such.

The apparatus can also comprise at least one pressure-determining device, which is set up to determine the pressure of the quantity of urine delivered to the urine test strip delivery zone or of one such quantity, in particular the pressure of the quantity of urine delivered by the feed element or by one such element. On the basis of the pressure which can be determined by such a pressure-determining device, i.e. the pressure of a quantity of urine delivered to the urine test strip delivery zone, it is possible to draw conclusions concerning the presence of gas bubbles, especially air bubbles, which may be present within the quantity of urine, which bubbles may possibly impair the information value of the detection data.

The invention also pertains to a urine test strip device, especially for an apparatus as described above, comprising at least one urine test strip with an analysis chamber comprising one analysis zone for the analysis of urine. At least a certain part of the urine test strip analysis zone is surrounded by at least one encapsulating element to form a fluid-tight encapsulation in at least a certain area.

The basic structure of the urine test strip device according to the invention comprises at least one urine test strip. The urine test strip comprises at least one analysis chamber, which comprises at least one analysis zone for the urinalysis. The analysis zone comprises at least one analysis reagent or is formed by at least one such agent.

The analysis reagent is generally a chemically reactive substance which brings about a chemical reaction on contact with urine such that an optically detectable change occurs in at least one optically detectable parameter. The optically detectable parameter of the chemically reactive substance, i.e., the analysis reagent, therefore changes in an optically detectable manner, i.e., through a change in its color, for example, and/or through a change in the color intensity, as a function of the composition of the quantity of urine contacting this substance. Thus the color, the color intensity, or a change in the color of the analysis zone constitutes an optically detectable parameter of the analysis zone.

The urine test strip device according to the invention is characterized in particular by a fluid-tight encapsulation of at least a certain part of the analysis zone, in particular by a complete encapsulation. The encapsulation is realized by at least one encapsulating element, which surrounds the analysis zone or a certain section of the analysis zone. Depending on the arrangement and geometric form of the encapsulating element, a certain gap can be formed between the element and the analysis zone; this gap then forms the urine test strip analysis chamber or a part thereof. Correspondingly, the encapsulating element can form the boundary of at least part of the urine test strip analysis chamber.

In all cases, the analysis zone, which is possibly applied to, or formed on, a carrier element, is therefore protected by the encapsulating element or by one such element from external influences which might impair the quality of a corresponding analysis reagent, which, on contact with urine, brings about an optically detectable change in an optically detectable parameter, i.e., for example, a color change. External influences of the type in question are in particular those caused by moisture and wetness, because these can lead to a degradation of the corresponding analysis zones and/or of the corresponding analysis reagents forming these zones. In this way, the urine test strip device according to the invention also deals with the previously encountered problem of the long-term storage of urine test strips, during which it has so far been extremely difficult to prevent a degradation of the analysis zones. Corresponding external influences can also take the form of mechanical effects, which can lead to damage to the analysis zone if it is not encapsulated appropriately.

An "encapsulating element" can also be understood as a multi-part, in particular multi-layered or multi-ply, structure. This can be advisable especially when a fluid-tight encapsulation against chemically different fluids is to be realized, so that certain layers or plies of the encapsulating element make possible a targeted encapsulation against specific fluids.

The analysis zone is advisably formed between a delivery zone for delivering a certain quantity of fluid, in particular a quantity of urine, to the analysis chamber and a discharge zone for carrying away a certain quantity of fluid, especially a quantity of urine, from the analysis chamber. Advisably at least a certain area of the delivery zone and/or of the discharge zone is surrounded by the encapsulating element or by one such element to form a fluid-tight encapsulation at least in a certain area. It is therefore possible to realize not only an encapsulation of the analysis zone but also an encapsulation of the corresponding delivery and/or discharge zones communicating with or connected to the analysis zone.

To facilitate the introduction of a feed and/or discharge element into the corresponding delivery and/or discharge zones of the urine test strip, it is advisable for the delivery zone and/or the discharge zone to comprise a convexity, especially a convexity in the form of a dome or a hemispherical cap. In this way, it is also possible to facilitate the flow of fluid through the analysis chamber, which can improve the analysis and thus the information value of the urine test strip. Corresponding convexities, in particular dome-like or hemispherical cap-shaped convexities, can also be referred to or thought of as so-called "puncture eyes". As an alternative to dome-like or hemispherical cap-shaped geometries, a corresponding convexity could also have a conical, polyhedral, or cylindrical geometry, for example.

The encapsulating element can be divided into at least two encapsulating element sections. The at least two encapsulating element sections together form the encapsulating element. The encapsulating element can comprise an upper encapsulating element section surrounding the exposed surface of the analysis zone and a lower encapsulating element section surrounding a surface of the analysis zone facing away from the exposed surface of the analysis zone.

The upper and lower encapsulating sections can differ from each other with respect to, for example, their geometric dimensions, their shape, and their material. In particular, a corresponding upper encapsulating element can be a 3-dimensionally complex molded part, whereas a corresponding lower encapsulating element can be a flat, essentially 2-dimensional component, i.e., for example, a film.

At least certain parts of the upper encapsulating element section are typically formed out of a transparent material, especially a transparent plastic material. This is advisable for the reason that in this way it is possible to detect a change in an optically detectable parameter, i.e., a color change, for example, of the analysis zone. Therefore, the term "transparent" is to be understood in particular to mean that the upper encapsulating element section allows detection of an optically detectable parameter. Suitable materials for forming the upper encapsulating element section include in particular transparent plastics such as PC and PMMA.

The lower encapsulating element section, in contrast, does not necessarily have to be made of transparent material. It is advisable here for the lower encapsulating element section, at least in the areas lying opposite the delivery zone and/or the discharge zone, to be provided with an elasticity such that it surrounds and forms a seal against certain sections of a feed and/or discharge element perforating and penetrating into the delivery and/or discharge zone. The lower encapsulating element section can therefore cling to the feed or discharge element penetrating into the delivery or discharge zone. In this way it can be ensured that no leakage occurs during the time that a certain quantity of urine is being delivered to or carried away from the urine test strip.

In particular, plastics such as PE and/or PET, for example, have the appropriate elasticity and are therefore suitable as materials for forming the lower encapsulating element section. The use of thermoplastic elastomers such as TPO and/or TPV, which, because of their structure, are characterized by comparatively high elasticity and thus have highly elastic properties, is also conceivable. The materials are typically in the form of films with a thickness in the range of 30-120 μm, especially in the range of 70-110 μm.

The elastic properties of corresponding films forming the lower encapsulating element section, i.e., in particular plastic films, can be influenced in targeted fashion during the production process or during processing by techniques such as stretching. To form the lower encapsulating element section, the use of metal foils or composite sheets formed out of composite materials consisting of different materials, e.g., plastic and metal, is also conceivable.

It is also advisable for the elasticity of the lower encapsulating element section to be high enough, at least in the areas lying opposite the delivery zone and/or the discharge zone, that a perforated area will be closed off and sealed by the areas of material of the lower encapsulating element section surrounding the perforation. At least certain areas of the lower encapsulating element section can therefore be configured as a septum or sealing membrane. The materials mentioned above, i.e., especially plastic material and composite materials, can be used to form the lower encapsulating element section It is advisable for the urine test strip device to comprise not only one but several urine test strips. The urine test strips are connected serially to each other in a strip-like or belt-like manner to form a set comprising several urine test strips. A corresponding set thus contains a plurality of urine test strips. This offers the first advantage that the apparatus according to the invention needs to be stocked with urine test strips only after comparatively long time intervals; the second advantage is that it is also possible to ensure the reliable operation of the apparatus over a comparatively long period of time. At the same time, the ease with which a set can be handled, i.e., the ease with which it can be rolled up onto a conveying device in the form of a transport roller and unrolled from it again, leads to practical advantages.

The connection or bond between one such urine test strip and the next can be formed in particular by the associated encapsulating elements, at least certain parts of which are connected to each other form continuous or discontinuous connection areas. The encapsulating elements can be connected to each other in the connection areas basically in either a positive, a nonpositive, or a permanently bonded manner. Concretely, the encapsulating elements of the associated urine test strips can be bonded together with an adhesive or welded together.

In the exemplary case in which the urine test strips are rectangular, the strips can be connected to each other along their long sides. Of course, in the case of urine test strips of appropriate shape, they can also be formed into a set by connecting them along their short sides. The location where the corresponding urine test strips are connected to each other is determined essentially by their basic shape, as a function of which suitably adapted connecting areas are to be selected. It is also necessary to take into consideration the way in which the sets of strips are stored and they way in which the urine test strips are supplied to the detection device of the apparatus.

The invention also pertains to a sanitary facility comprising a flush toilet, especially a wall-hung or floor-mounted unit, with a base body, especially of ceramic material, and with an apparatus as described above. In general, therefore, all embodiments of the apparatus are applicable in analogous fashion to any sanitary facility.

The sanitary facility according to the invention comprises a flush toilet of the wall-hung or floor-mounted type. The flush toilet is therefore attachable or mountable on a wall or a floor. The flush toilet comprises a base body, especially a ceramic base body. A properly installed base body will comprise in particular upper surface sections for the installation of a lid and/or seat part and inner surface sections, which form an inner area, into which a user can deposit excretions, i.e., in particular feces and urine.

With respect to the apparatus, the flush toilet comprises mounting or fastening areas for the mounting or fastening of the apparatus or of individual components of the apparatus. Basically, the apparatus, i.e., in particular a housing part possibly belonging to the apparatus, can be or is attached to the base body in a positive and/or nonpositive and/or permanently bonded manner. For this purpose, suitably adapted fastening means, which, for example, make it possible to establish a latching, a screwed, or an adhesively bonded connection of the apparatus to the flush toilet base body, are present in appropriate mounting or fastening areas of the flush toilet. Of course, appropriate fastening means can also be provided on the apparatus.

With respect to the concrete geometric structure of the base body, appropriate mounting or fastening areas on the flush toilet are advisably to be arranged in such a way that the apparatus is not visible to the user. For this purpose, cover elements in the form of faceplates, for example, can be provided, which make it possible to cover the apparatus. Appropriate cover elements can be held in place in the proper position relative to the base body of the flush toilet by suitably adapted fastening elements in the form of, for example, angle brackets.

So that a certain quantity of urine, which is to be analyzed by the apparatus, can be withdrawn, at least one withdrawal device is configured or arranged in the base body. The withdrawal device comprises at least one tubular element, arranged in an opening in the base body, which tubular element is supported so that it can move relative to a closing element between an open position and closed position. The closing element is typically permanently arranged or mounted on the base body. In the open position, fluid can flow through the tubular element. The closed position is therefore defined by the inability of fluid to flow through this tubular element. A certain quantity of urine can therefore be withdrawn by means of a coordinated control of the movement of the tubular element toward the closing element, which can be realized by, for example, moving the tubular element into the open position and then, after a certain period of time, e.g., an interval of 1-5 seconds, moving the tubular element back into the closed position.

The movements of the tubular element are advisably realized by a drive device coupled to the element. The drive device can move the tubular element in particular between the open position and the closed position. The drive device comprises for this purpose, for example, a magnetic drive, i.e., for example a rotary magnet, or a motorized drive, i.e., for example, an electric motor, or is configured as such. So that the tubular element can be moved into the closed position and/or to support the movement of the tubular element into the closed position, furthermore, spring elements can be provided, by means of which force can be exerted on the tubular element to move it into the closed position or to ensure that it is reliably moved into the closed position.

Of course, the inverse kinematic relationship is also possible in principle, according to which a movably supported closing element can be moved between an open position and a closed position relative to a tubular element permanently arranged on or fastened to the base body.

The withdrawal device, i.e., in particular the closing element belonging to it, is typically arranged in such a way that at least a certain part of it projects into corresponding inner surface sections of the base body. In the closed position, the withdrawal device, i.e., in particular the closing element belonging to it, is typically flush with the inner surface surfaces of the base body, so that an (essentially) uniform surface is obtained.

The tubular element is typically connected to a feed line leading to the feed and discharge device of the apparatus by means of a connecting line, through which a quantity of urine withdrawn by the withdrawal device can be conducted into the feed and discharge device and onward from there to a urine test strip analysis chamber. In corresponding fashion, the tubular element advisably comprises, on or in the area of its free end facing away from the base body, a connector element, so that it can be connected to the feed and discharge device of the apparatus or to one such device.

At least one tank can be installed in a feed line leading to a corresponding feed and discharge device of the apparatus; a certain quantity of urine, e.g., approximately 200 mL, can be collected and held in this tank before the urine is actually delivered to the feed and discharge device of the apparatus. The tank or a corresponding tank is therefore installed between the withdrawal device and the feed and discharge device of the apparatus. The tank or a corresponding tank can be provided with at least one vent device and/or at least one level indicator device. A vent device can, for example, comprise a vent valve or be configured as such. A level indicator device can, for example, comprise a level sensor and/or be configured as such.

After the urine has been analyzed, it is a sensible idea to conduct it back into the flush toilet and so that it can be sent to the drain pipe of the flush toilet. Correspondingly, it is advisable for a discharge line leading from the discharge device of the apparatus or from one such discharge device to lead into an interior space enclosed by the base body. The interior space of the base body comprises appropriate internal surface base body sections.

The sanitary facility, i.e., the flush toilet belonging to it, comprises typically at least one flushing device for performing the flushing operation of the flush toilet. It is advisable for at least one fluid line of the flushing device to be connectable or connected to a feed line leading to a feed device of the apparatus. In this way it is possible to realize flushing or cleaning operations of the apparatus, which, for example, is a sensible way to prevent the undesirable formation of deposits and/or odors.

In addition to the flushing device, the sanitary device, i.e., the flush toilet belonging to it, can also comprise a shower device, by means of which, after the sanitary facility has been used, it is possible to clean certain body areas of the user. Correspondingly, a drying device can also be provided, which makes it possible for areas of the user's body cleaned by the shower device to be dried.

Additional advantages, features, and details of the invention can be derived from the exemplary embodiments described in the following and from the drawings:

DETAILED DESCRIPTION OF THE INVENTION

Figure 1:
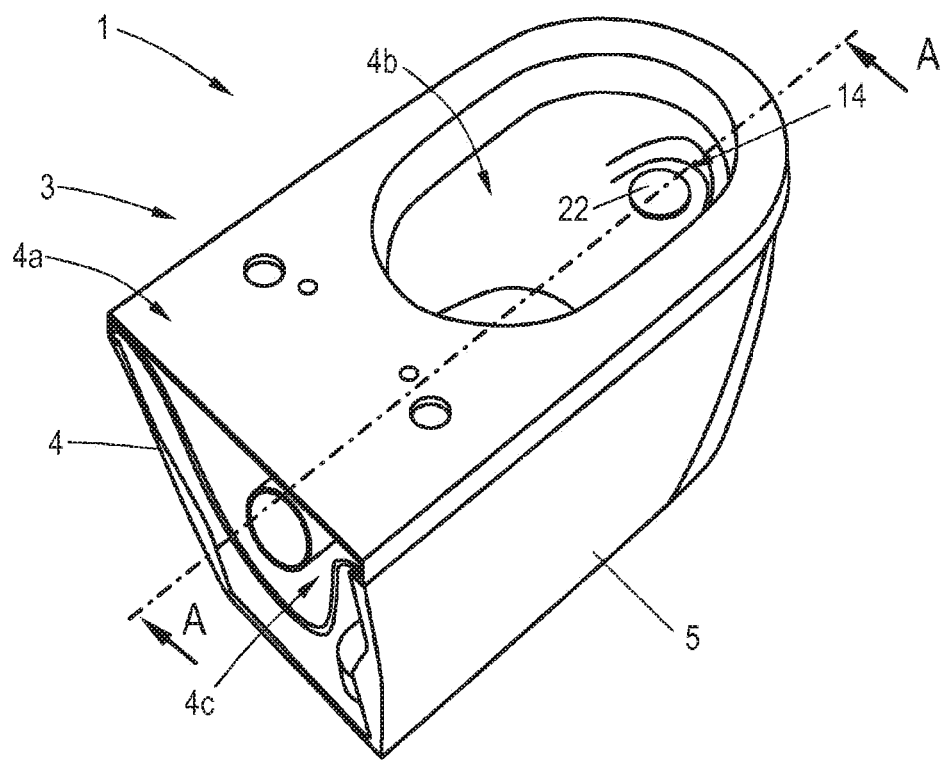
FIGS. 1-5 show schematic diagrams of a sanitary facility according to an exemplary embodiment of the invention.
Figure 2:
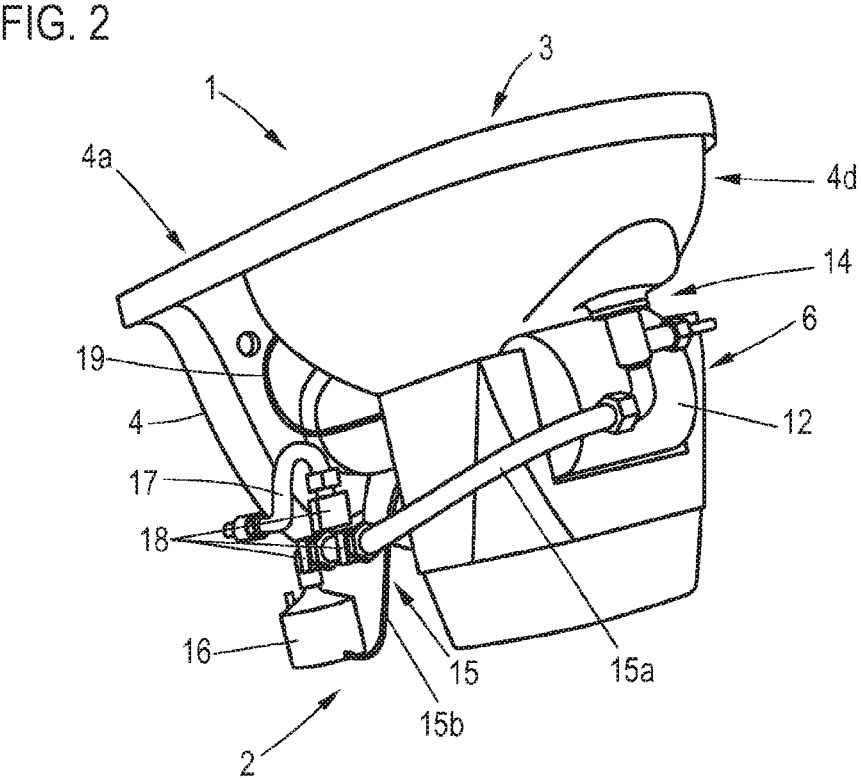
Figure 3:
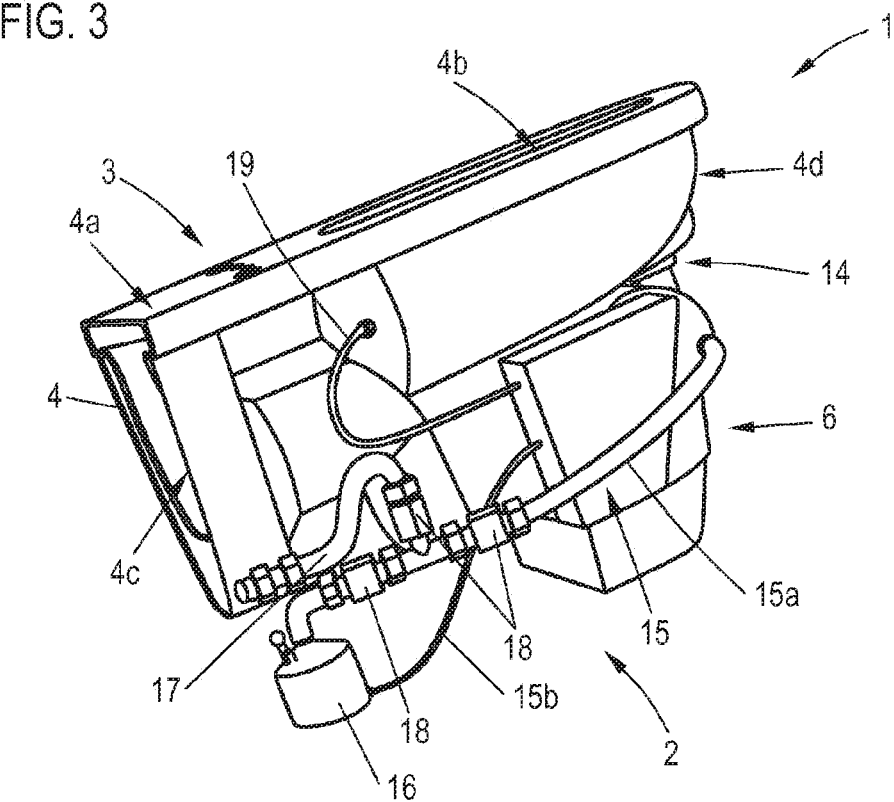
Figure 4:
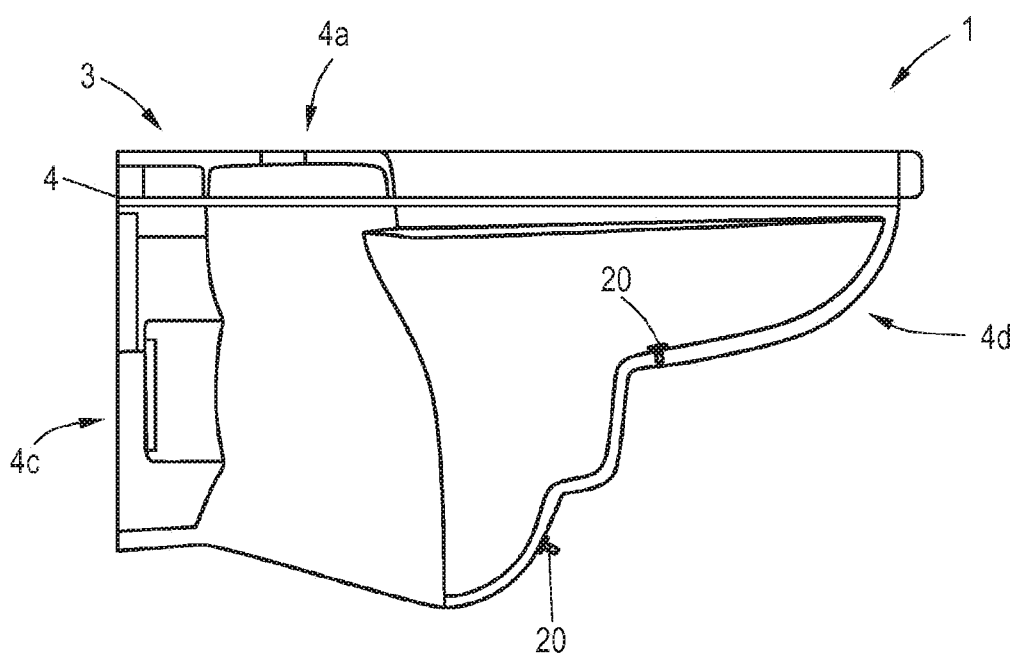
Figure 5:
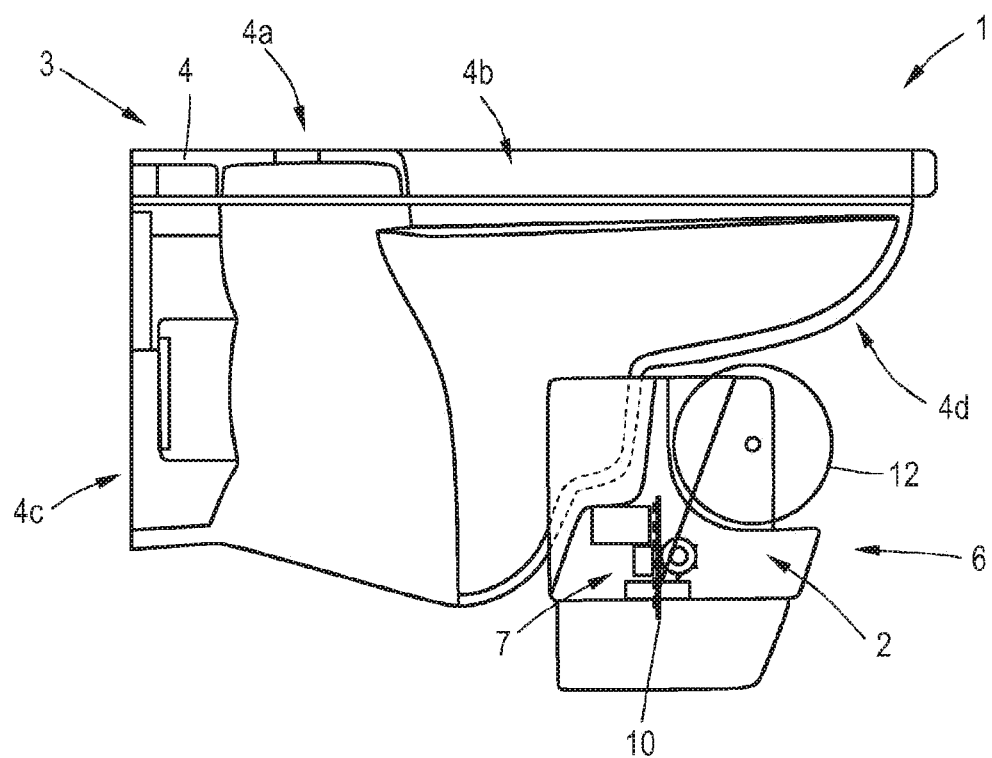

Each of FIGS. 1-15 shows a schematic diagram of a sanitary facility 1 according to an exemplary embodiment of the invention. FIGS. 1-3 show perspective views, and FIGS. 4-5 show cross-sectional views of the sanitary facility 1. The direction in which the cross section is taken and the viewing direction are indicated in FIG. 1 by the general cross-sectional line A-A. The sanitary facility 1 is equipped with an apparatus 2 for the analysis of urine. The integration of an apparatus 2 of this type into the sanitary facility makes it easy to conduct an analysis or examination of urine discharged into the sanitary facility 1 or of other body fluids.

The sanitary facility 1 comprises a floor-mounted or wall-hung flush toilet 3. The flush toilet 3 comprises a ceramic base body 4. The base body 4 comprises various surface sections, of which only the surface sections 4a-4d are described in detail below. With respect to a properly installed base body 4, this base body comprises upper surface sections 4a for the mounting of a lid and/or seat part (not shown), inner surface sections 4b, which form the boundaries of an inner, bowl-like area, into which a user can deposit excretions or body fluids, i.e., especially feces and urine; rear surface sections 4c, which make it possible to establish a connection to a pipeline (not shown) connected to a sewer; and front surface sections 4d.

The apparatus 2 is not visible in FIG. 1, because it is located behind a cover element 5 in the form of a ceramic faceplate. The cover element 5 can be held in place and in the proper position relative to the base body 4 of the flush toilet by means of suitably adapted fastening elements (not shown) in the form of, for example, angle brackets. In FIGS. 2 and 3 the cover element 5 has been removed, so that the apparatus 2, i.e., the components belonging to it, can be recognized.

FIGS. 4-5 show the apparatus 2, i.e., the housing part 6, belonging to it, in or on which the essential components or functional elements of the apparatus are accommodated or supported; the corresponding cover element 5 has been removed.

The essential parts or functional components of the apparatus 2 include a feed and discharge device 7, which is set up to deliver a certain quantity of urine to an analysis chamber 9, comprising at least one analysis zone 8, of a urine test strip 10 and to carry away a certain quantity of urine from an analysis chamber 9, comprising an analysis zone 8, of a urine test strip 10 or of one such test strip. The structure and function of the feed and discharge device 7 will be described in greater detail below on the basis of FIGS. 7-10 in particular.

The essential parts or functional components of the apparatus 2 also include a detection device 11, which is set up to detect a change in at least one optically detectable parameter in at least a certain area of the corresponding analysis zone 8 or of one such zone of the urine test strip 10 or of one such strip. The optically detectable parameter changes in an optically detectable manner as a function of the composition of a quantity of urine contacting a corresponding urine test strip analysis zone 8, i.e., for example, by a change in its color and/or by a change in its color intensity. Thus the color or color intensity, for example, of the analysis zone 8 is a corresponding optically detectable parameter. The detection device 11 is also set up to generate detection data, which describe at least one such optically detectable or detected parameter of an analysis zone 8 or a describe change in such a zone. So that the detection device 11 can detect a corresponding change in an optically detectable parameter, it comprises detection means in the form of optical scanners. The function of the detection device 11 will be described in greater detail below, especially in conjunction with FIGS. 7-10.

As can be derived especially clearly from FIGS. 2 and 5, a conveying device 12 in the form of a transport roller is rotatably supported on the housing part 6 of the apparatus 2. The conveying device 12 is set up to convey at least one urine test strip 10 into a defined detection zone of the apparatus, in which it is possible for the detection device 11 to detect a change in a corresponding optically detectable parameter in at least a certain area of a urine test strip analysis zone 8 and/or to convey the strip out of such a detection zone. A set 13 of several strip-like or belt-like urine test strips 10, which are serially connected to each other, can be unrolled from the conveying device 12 configured as a transport roller or rolled up onto the conveying device 12 configured as a transport roller; this set of test strips will be described in greater detail below in conjunction with FIG. 13.

FIG. 1 also shows a withdrawal device 14 on the base body of the flush toilet. The withdrawal device 14 is arranged inside an opening in the area of the inner surface sections 4b of the base body 4. The withdrawal device 14 serves to withdraw a certain quantity of urine while a user is urinating into the flush toilet 3, this quantity then being sent to the apparatus 2 for analysis. The structure and function of the withdrawal device 14 is described in greater detail with reference to FIG. 6.

On the basis of FIGS. 2 and 3 it can be seen that a first line section 15a of a feed line 15 of the feed and discharge device 7 of the apparatus leads to a tank 16. A tank 16 is therefore installed in a feed line 15 leading to the apparatus 2, in which tank a certain quantity of urine, e.g., approximately 200 mL, can be collected and held before the sample is actually delivered to the apparatus 2, i.e., to the feed and discharge device 7 of the apparatus. The tank 16 is therefore inserted between the withdrawal device 14 and the feed and discharge device 7 of the apparatus. The tank 16 is equipped with a vent device (not shown) in the form of a vent valve and with a level indicator device (not shown) in the form of a level sensor.

Proceeding from the tank 16, a second line section 15b of the feed line 15 leads to the feed and discharge device 7 of the apparatus. The first line section 15a of the feed line 15 is, for example, a flexible textile hose, and the second line section 15b of the feed line 15 is, for example, a length of laboratory tubing with a diameter smaller than that of the textile hose or of one such hose.

Figure 14:
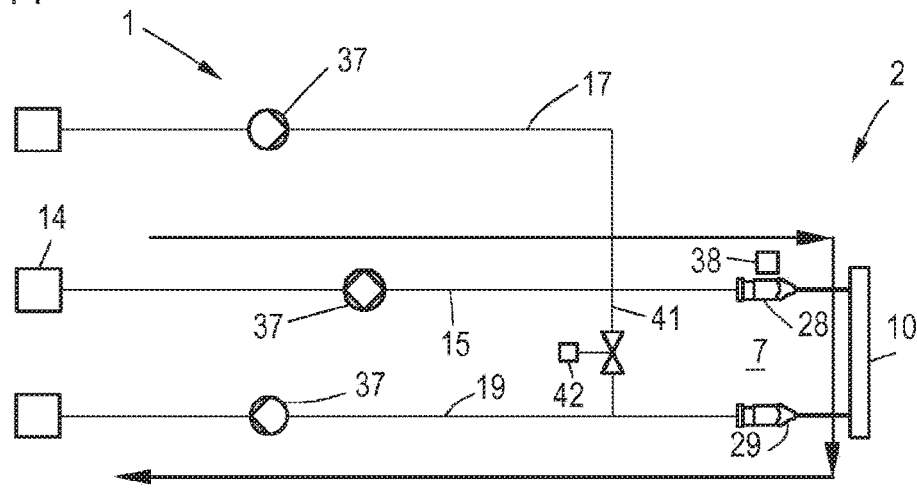
FIGS. 14-19 show schematic diagrams of various operating modes of a sanitary facility according to an exemplary embodiment of the invention.

As can be seen, a fresh water line 17 connected to a flushing device 43 of the flush toilet opens out into the first line section 15b of the feed line 15 (compare FIG. 14 ff). Both upstream and downstream of the connection of the fresh water line 17 to the feed line 15, a valve device 18, e.g., in the form of a magnetic valve, is installed in the first line section 15a of the feed line 15, i.e., on the feed side. A corresponding valve device 18 is also installed on the fresh water feed line side upstream of the connection area.

On the basis of FIGS. 2 and 3 it can also be seen that a discharge line 19 leads from the apparatus 2, i.e., in particular from the feed and discharge device 7 of the apparatus arranged on the housing part 6, to the interior space of the flush toilet 3 bounded by the inner surface sections 4b of the base body 2. Thus, after the urine has been analyzed by the apparatus 2, it is possible to return the urine to the flush toilet 3 and thus to send it to the drain pipe of the flush toilet. The discharge line 19 can also be a length of laboratory tubing.

The detachable mounting of the housing part 6 of the apparatus on the base body 4 of the flush toilet will now be explained on the basis of FIGS. 4 and 5. FIG. 4 shows the base body 4 of the flush toilet before the housing part 6 is attached to it. FIG. 5 shows the base body 4 of the flush toilet after the housing part 6 has been attached. As can be seen in FIG. 4, the base body 4 is provided in the area of the exposed front surface sections 4d with fastening elements 20. The fastening elements 20 are attached to the base body 4 by means of, for example, an adhesive. The fastening elements 20 comprise threaded bolt-like fastening sections (not shown in detail), on which the housing part 6 can be mounted in a nonpositive manner, i.e., in particular by means of a screw joint. Of course, the housing part 6 comprises corresponding threaded receptacles or holes to make such attachment possible, i.e., for example, for the screw joint. Typically three corresponding fastening elements 20 are provided on the base body, which make it possible to obtain a three-point mounting of the housing part 6 on the base body 4.

Figure 6:
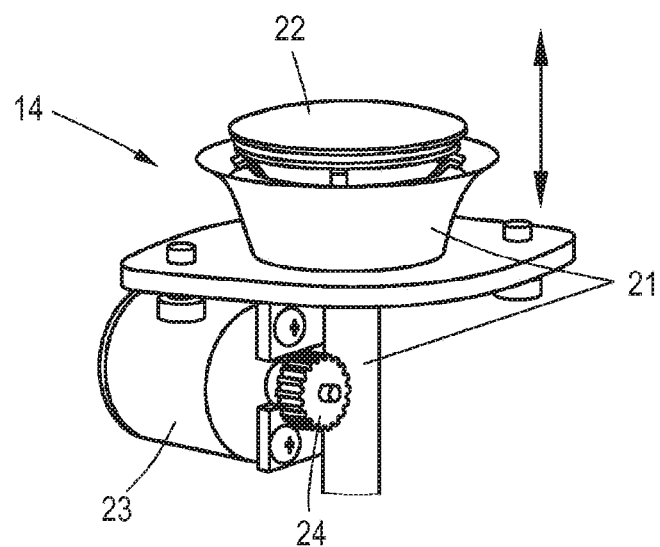
FIG. 6 shows a schematic diagram of a withdrawal device of a sanitary facility according to an exemplary embodiment of the invention.

FIG. 6 shows a schematic diagram of a withdrawal device 14 of the sanitary facility 1 or one such facility according to an exemplary embodiment of the invention. The withdrawal device 14, an isolated view of which is shown in FIG. 6, comprises a hollow-cylindrical, tubular element 21 passing through an opening in the base body 4; this tubular element is supported in such a way that it can be moved relative to a permanently mounted, disk-shaped closing element 22 on the base body and thus between an open position and closed position. The ability of the tubular element 21 to move between the open position and the closed position is indicated in FIG. 6 by the double arrow.

In the open position shown in FIG. 6, the tubular element 21, which has a funnel-shaped section forming the free end of the tubular element 21, has been moved away from the closing element 22 in such a way that urine can flow from the interior of the base body 4 in, i.e., through, the tubular element 21 and thus arrive in the first line section 15a of the feed line 15 to the feed and discharge device 7, this first line section being connected downstream from the withdrawal device 14. For this purpose, the tubular element 21 comprises on or in the area of its free end facing away from the base body 4 a connecting means (not shown) for establishing a connection to the feed line 15 leading to the feed and discharge device 7. A screen can be present in the connecting means or upstream from the connecting means.

When in the closed position, the tubular element 21 creates a sealing effect through its contact with the closing element 22. In other words, the tubular element 21, when in the closed position, rests against the closing element 22 to create a seal. This seal-producing contact is supported by a sealing element, e.g., in the form of an O-ring (not shown in detail), arranged around the outer circumference of the closing element 22.

Movements of the tubular element 21 are realized by means of a drive device 23 connected to it; this drive device can move the tubular element 21 in particular between the open position and the closed position. The drive device 23 comprises for this purpose, for example, a magnetic drive in the form of a rotary magnet coupled to the tubular element 21 by means of a pinion or gear wheel element 24. So that the tubular element 21 can be moved into the closed position or so that the movement of the tubular element 21 into the closed position can be supported, a spring (not shown) can be provided, by means of which an elastic force can be applied to the tubular element 21, i.e., a force which moves the tubular element into the closed position or reliably ensures that it will assume this closed position.

Figure 7:
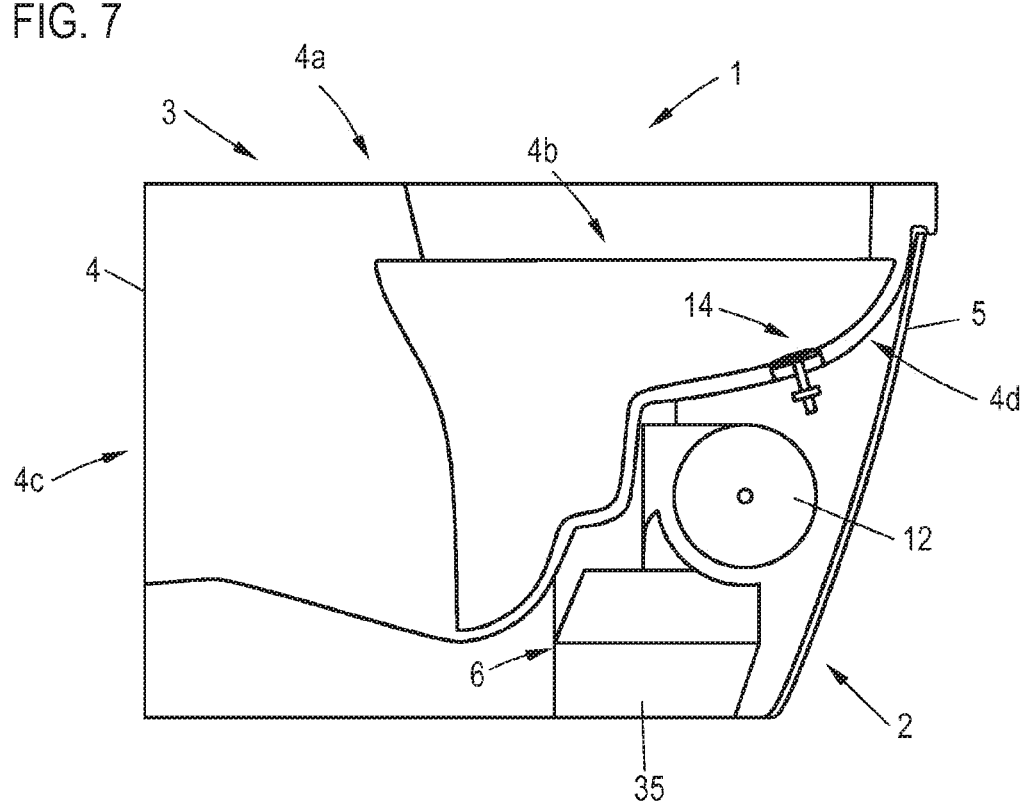
FIGS. 7-10 show schematic diagrams of an apparatus for analyzing urine according to an exemplary embodiment of the invention.
Figure 8:
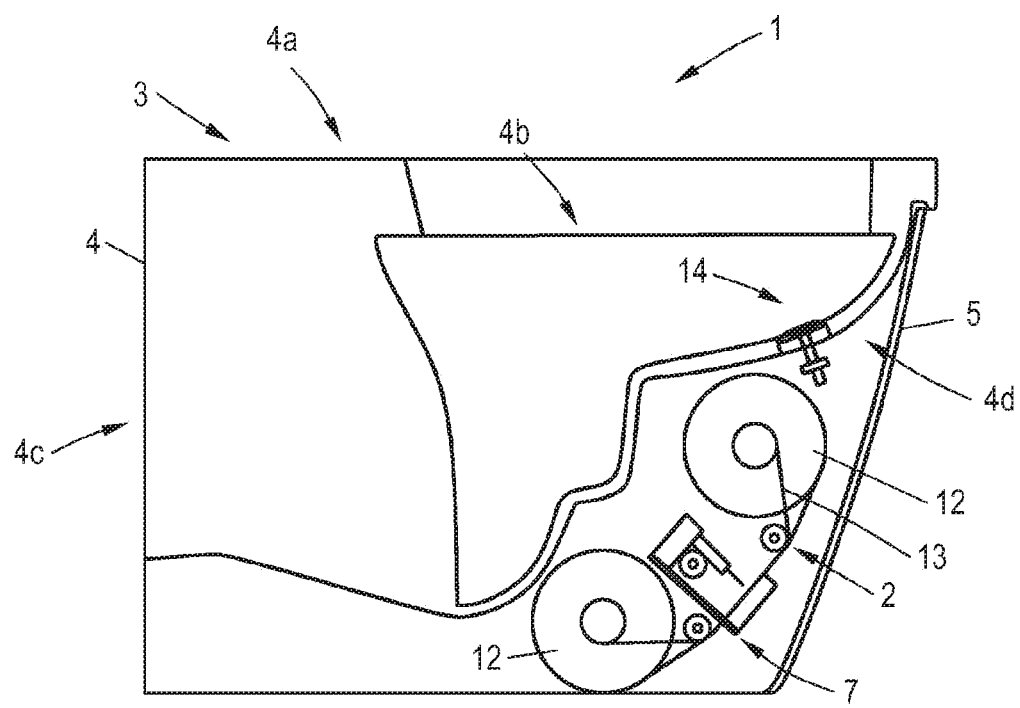
Figure 9:
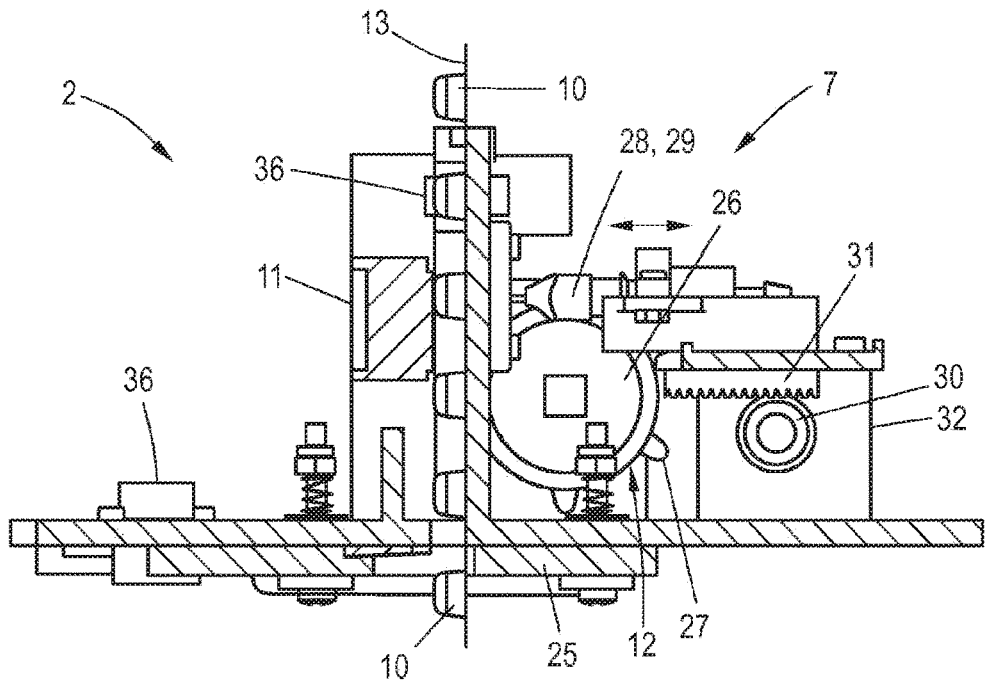
Figure 10:
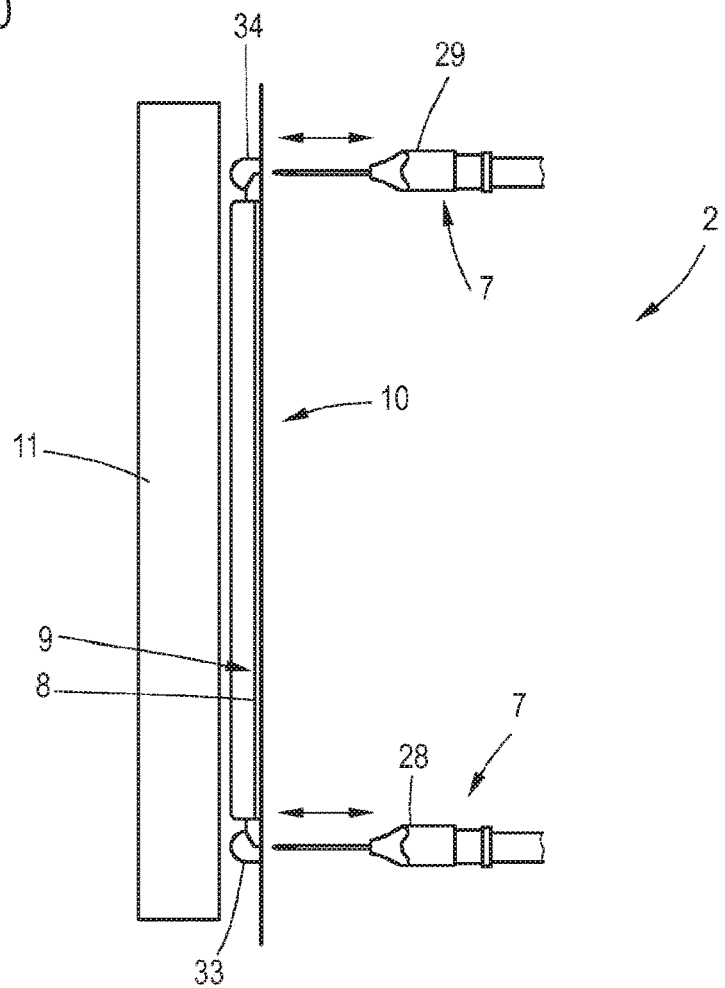

FIGS. 7-10 show schematic diagrams of an apparatus 2 for analyzing urine according to an exemplary embodiment of the invention. FIGS. 7 and 8 show cross-sectional views of two different exemplary embodiments of an apparatus 2 mounted on a flush toilet; FIG. 9 shows an enlarged partial view of the apparatus 2 according to the exemplary embodiment of FIG. 7; and FIG. 10 shows an enlarged partial view of the apparatus 2 from above.

In regard to the exemplary embodiment shown in FIG. 7, it should be pointed out that the housing part 6 on the apparatus has a 3-dimensional geometric shape slightly different from that shown in FIG. 3, which illustrates that there is in principle a certain freedom with which the apparatus 1, i.e., the components belonging to it, can be designed.

The essential difference between the two exemplary embodiments of the apparatus 2 shown in FIGS. 7 and 8 consists in the number of transport rollers belonging to the conveying device 12. In the exemplary embodiment according to FIG. 7, only one conveying device 12 with a single transport roller, from which a corresponding set 13 of several serially connected strip-like or belt-like urine test strips 10 can be unrolled, is present; in contrast, in the exemplary embodiment shown in FIG. 8, a conveying device 12 is provided with two transport rollers and also with deflection rollers, upstream and downstream from the transport rollers, the diameters of the deflection rollers in the exemplary embodiment being smaller than those of the transport rollers. Correspondingly, in the exemplary embodiment shown in FIG. 8, it is possible for a set 13 of several serially connected strip-like or belt-like urine test strips to be unrolled from a first transport roller in such a way that at least one urine test strip 10 to be conveyed into the detection zone of the detection device 11 can be or is moved into the detection zone and can be rolled up onto a second transport roller in such a way that it can be or is moved out of the detection zone.

In the exemplary embodiment shown in FIG. 7, a separation device 25 downstream from the detection device 11 is provided (compare FIG. 9), which is set up to separate at least one urine test strip 10 from the set 13 of several strip-like or belt-like connection urine test strips 10. By means of the separation device 25, individual or several used urine test strips 10 can be separated from the set and thus handled independently, i.e., can be disposed of. The separation device 25 comprises for this purpose a blade, for example, or a laser (not shown in detail).

Urine test strips 10 which have been separated from the set 13 can be received by and collected in a receiving section 35, which serves to receive used urine test strips 10, i.e., in particular test strips which have been in the meantime treated with a certain quantity of urine, and is mounted detachably on the housing part 6.

FIG. 9 shows an enlarged view of the exemplary embodiment of the apparatus 2 shown in FIG. 7. As can be seen, a corresponding set 13 of serially connected urine test strips 10 extends between the gap formed between the detection device 11 and the feed and discharge device 7 and thus through a corresponding detection zone of the detection device 11. The guidance and positioning of the set 13 is assisted by a rotatably supported pimple wheel 26, which also forms part of the conveying device 12. The pimple wheel 26 comprises conveying sections formed by radially projecting pimples 27, arranged a certain distance apart around the circumference, to convey at least one urine test strip 10. The rotation of the pimple wheel 26 can transport the urine test strips 10 continuously or discontinuously through the detection zone.

On the basis of FIGS. 9 and 10 it can be seen that the feed and discharge device 7 comprises a cannula-like feed element 28 capable of moving in linear or translational fashion and a cannula-like discharge element 29, movably supported in corresponding fashion. The feed element 28 serves to deliver a certain quantity of urine to a delivery zone 33 of an analysis chamber 9 of a urine test strip 10, whereas the discharge element 29 serves to carry away a certain quantity of urine from a discharge zone 34 of an analysis chamber 9 of a urine test strip 10.

To realize movements of the feed element 28 and of the discharge element 29, the feed and discharge device 7 comprises a drive device 32 connected to them. The drive device 32 comprises an electric motor (not shown). The drive device 32 makes it possible to move the feed or discharge element 28, 29 toward the delivery zone 33 or the discharge zone 34 of the urine test strip or toward one such delivery or discharge zone in such a way that the cannula-like tip of the feed or discharge element 28, 29 penetrates into the delivery and/or discharge zone 33, 34 of the urine test strip and thus delivers or carries away a certain quantity of urine into or out of the analysis chamber 9 of the urine test strip. The movable support and thus the axis of the movement of the feed element 28 and of the discharge element 29 are indicated by the double arrow.

It can be seen that the drive device 32 is connected by several components such as a gear wheel 30 and a toothed rack 32 meshing with it to the feed and discharge element 28, 29, so that rotational movements of a take-off shaft (not shown) of the drive device can be converted by the gear wheel 30 and the toothed rack 31 into translational movements of the feed element 28 and of the discharge element 29.

The apparatus 2 is also equipped with a position-determining device 36 arranged above the detection device 11; this position-determining device is set up to determine the position of a urine test strip 10 as it pertains to the detection of a corresponding optically detectable parameter of an analysis zone 8 of the urine test strip, e.g., to the detection of a change in such a parameter, by means of the detection device 11. Another position-determining device 36, arranged underneath the detection device 11, is set up to determine a starting position of the separation device 25. The starting position of the separation device 25 is defined as the position in which no separation of a urine test strip 10 from the set 13 occurs. Each of the position-determining devices 36 comprises light barriers for the stated purposes.

Although not visible in FIGS. 7-10, the apparatus 2 also comprises a pump device 37 installed in a feed line 15 leading to the feed element 28, and a pump device 37 installed in a discharge line leading from a discharge element 29. The pump devices 37 are illustrated schematically, however, in FIG. 14 ff. The pump devices 37, which can be, for example, small centrifugal pumps, serve in particular to convey urine through the apparatus 2, i.e., in particular to convey, i.e., to pump, it into a corresponding urine test strip analysis chamber 9 and to convey, i.e., to pump, it from a corresponding urine test strip analysis chamber 9.

The apparatus 2 is also equipped with a pressure-determining device 38, which is set up to determine the pressure of a quantity of urine delivered to the urine test strip delivery zone 33; it determines, for example, the pressure of the quantity of urine supplied through the feed element 28. The pressure-determining device 38 comprises for this purpose suitably adapted pressure sensors. The pressure-determining device 38 is also represented schematically in FIG. 14 *ff*. On the basis of the pressure of a quantity of urine supplied to the urine test strip delivery zone 33 which can be determined by such a pressure-determining device 38, conclusions can be drawn concerning any gas bubbles which may be present, especially air bubbles, within the quantity of urine, which bubbles may possibly impair the information value of the detection data.

The apparatus 2 also comprises a bypass line 41, shown schematically in FIG. 14 *ff*, which connects the feed line 15 leading to a feed element 28 and a discharge line 19 leading to a discharge element 29. A valve device 42 for opening and closing the bypass line 41 is installed in the bypass line 41.

FIG. 10 shows an enlarged, partial view, from above, of the apparatus 2. In FIG. 10, one can see the movable support of the feed and discharge elements 28, 29 belonging to the feed and discharge device 7, as indicated again by a double arrow. In the diagram of FIG. 10, the feed and discharge elements 28, 29, which typically are driven, i.e., moved, simultaneously and uniformly, are a certain distance away from the urine test strip 10, i.e., from a corresponding urine test strip delivery zone 33 and a urine test strip discharge zone 34. The delivery or discharge of a certain quantity of urine to the urine test strip analysis chamber 9 is not possible until the feed element 28 has penetrated into the urine test strip delivery zone 33 and the discharge element 29 has penetrated into the urine test strip discharge zone 34. As can be seen, the urine test strip delivery zone 33 and the urine test strip discharge zone 34 are defined in structural terms by a dome-shaped or hemispherical cap-like convexity.

Figure 11:
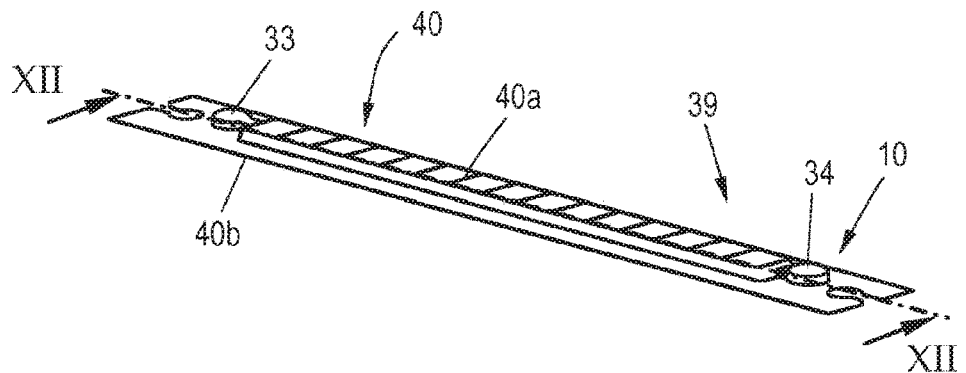
FIGS. 11-13 show schematic diagrams of a urine test strip device according to an exemplary embodiment of the invention.
Figure 12:
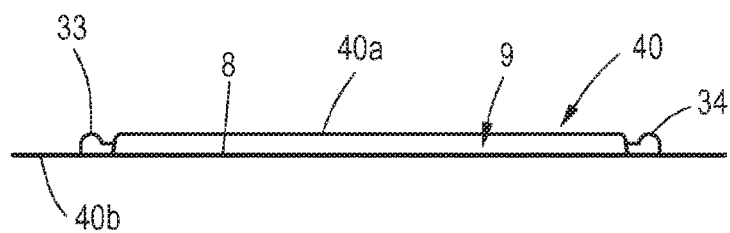
Figure 13:
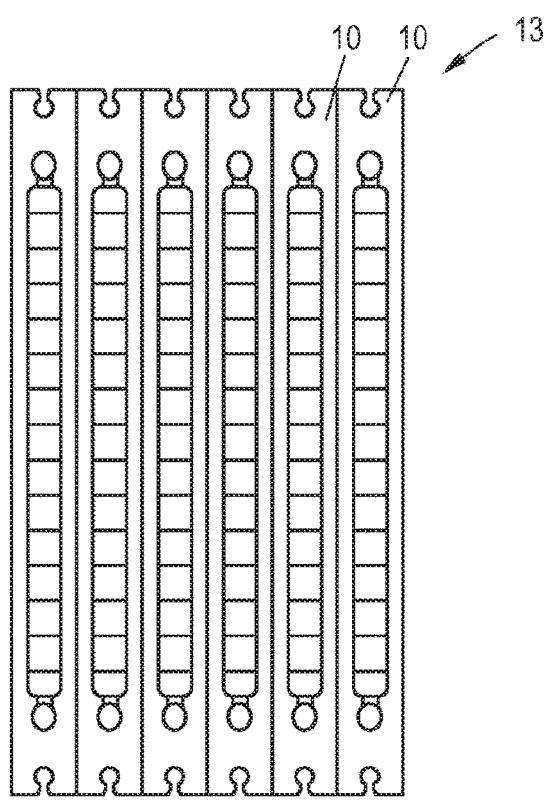

The other components of a urine test strip 10 forming part of a urine test strip device 39 are described below with reference to FIGS. 11-13, each of which shows a schematic diagram of a urine test strip device 39 according to an exemplary embodiment of the invention. FIG. 11 shows a perspective view of single urine test strip 10; FIG. 12 shows a cross-sectional view along the line XII-XII of FIG. 11; and FIG. 13 shows a view from above of a set 13 of several serially connected strip-like or belt-like urine test strips 10.

It can be seen in FIG. 11 that a single urine test strip 10 typically has a rectangular outline. An analysis chamber 9 comprising an analysis zone 8 for the urinalysis is located between an upper encapsulating element section 40*a* and a lower encapsulating element 40*b*. The upper encapsulating element section 40*a* and the lower encapsulating element section 40*b* form together an encapsulating element 40, by which the analysis zone 8 is encapsulated and thus protected from external influences, i.e., in particular from moisture.

The upper encapsulating element section 40*a* is configured as a complex 3-dimensional molded part and comprises an essentially flat middle wall section forming the boundary of the analysis chamber 9 and two dome-like or hemispherical cap-like lateral wall sections forming the boundary of the delivery zone 33 and the discharge zone 34. Of course, there is a passage between the delivery and discharge zones 33, 34 and the analysis chamber 8, which means that the two zones communicate with each other.

The upper encapsulating element section 40*a* is made of a transparent plastic material such as PC. The plastic material is so transparent that a change in an optically detectable parameter of the analysis zone 8, i.e., a color change, for example, can be detected by the detection device 11.

The lower encapsulating element section 40*b* does not have a complex 3-dimensional shape but is rather flat or sheet-like. The lower encapsulating element section 40*b* thus represents a flat part or a film. Its thickness is typically in the range of 30-120 µm, especially in the range of 70-100 µm.

The lower encapsulating element 40*b* is made of an elastic plastic material such as PE or PET, for example, or of a plastic composite material. With respect to the elastic properties, the lower encapsulating element section 40*b* can also be made out of a thermoplastic elastomer, i.e., TPO and/or TPV, for example.

The elastic properties of the lower encapsulating element section 40*b* make it possible for a certain area of a feed or discharge element 28, 29 which has penetrated into and thus perforated the delivery or discharge zone 33, 34 to be surrounded with a sealing action. The lower encapsulating element section 40*b* therefore clings closely to a feed or discharge element 28, 29 which is penetrating or has penetrated into the delivery or discharge zone 33, 34, which ensures that no leakage occurs while a certain quantity of urine is being delivered to or carried away from the urine test strip 10.

The elastic properties of the lower encapsulating element section 40*b* also make it possible for a perforated area to be or to become sealed off by the areas of material surrounding it. The lower encapsulating element section 40*b* thus also serves as a septum or as a sealing membrane, as a result of which it is ensured that no leakage occurs even after a certain quantity of urine has been delivered to or carried away from the urine test strip 10.

FIG. 13 shows a set 13 of several urine test strips 10. The urine test strips 10 are connected to each other to form a strip or belt. The set 13 can thus be referred to as or considered a strip comprising several urine test strips 10 or as a belt comprising several urine test strips 10. As can be seen, the urine test strips 10 are connected to each other along their long sides. The connection between corresponding urine test strips 10 is formed in particular by the associated encapsulating elements 40, at least certain areas of which are connected to each other to form continuous or discontinuous connection areas. The encapsulating elements 40 of adjacent urine test strips 10 can be bonded together with an adhesive or welded together.

On the basis of FIGS. 14-19, which show schematic diagrams of various operating modes of a sanitary facility 1 according to an exemplary embodiment of the invention, various exemplary embodiments of a method for the operation of a sanitary facility 1 with an apparatus 2 belonging to it are described below. The description of the operating modes is based on a configuration of the sanitary facility 1, i.e., of the apparatus 2, illustrated in FIG. 14 *ff* as described above. Fluid flows are indicated generally in FIG. 14 *ff*. by arrows. A pump device of the flushing device is also indicated by the reference number 37.

FIG. 14 shows by way of example an operating mode for the realization of a withdrawal of a certain quantity of urine and for an analysis of it, i.e., in particular for the acquisition of corresponding detection data. The quantity of urine withdrawn by the withdrawal device 14 is conveyed or pumped by the pump device 37 through the feed line 15 into the urine test strip 10, i.e., over the analysis zone 8 and thus through the analysis chamber 9. The quantity of urine is then, i.e., in particular after the analysis and the generation of the detection data, conveyed or pumped out of the urine test strip 10 and from the apparatus 2 via the discharge line 19. Of course, the corresponding feed elements 28 or discharge elements 29 of the apparatus have previously penetrated into urine test strip delivery or discharge zones 33, 34. The valve device 42 installed in the bypass line 41 is closed during this phase. The detection device 11 generates a corresponding set of detection data, which, as will be described further below, is transmitted to an evaluation device (not shown), integrated into the apparatus 2 or arranged externally, i.e., spatially separated from the apparatus 2.

Figure 15:
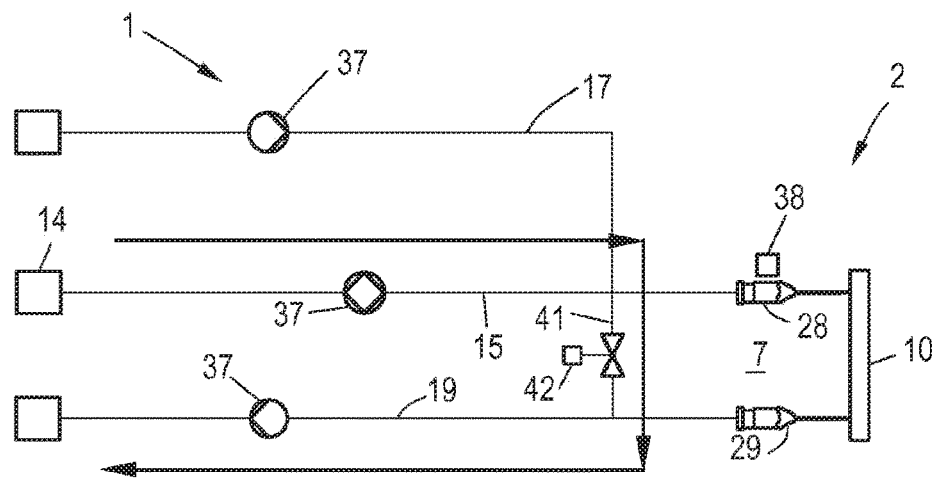

FIG. 15 shows by way of example an operating mode for the realization of an emptying of the feed line 15 and of the discharge line 19. The valve device 42 installed in the bypass line 41 is opened in this phase, so that any residual quantities of urine which may be present in the feed line 15 or in the discharge line 19 can be pumped away.

Figure 16:
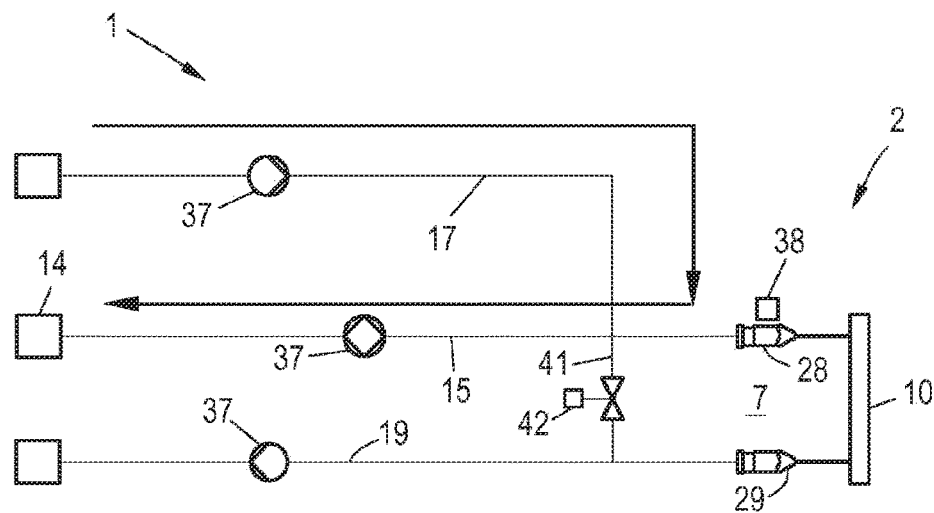

FIG. 16 shows by way of example an operating mode for the realization of a flushing of the feed line 15 and of the withdrawal device 14 upstream of it. As can be seen, flushing fluid, in particular water provided by the fresh water feed line 17, is conveyed, i.e., pumped, through the feed line 15 and through the withdrawal device 14 by a flushing device 43 of the flush toilet. The valve devices 18 and the valve device 42 installed in the bypass line 41 are closed during this phase, so that the flushing fluid cannot flow into either the feed and discharge device 7 or into the discharge line 19.

Figure 17:
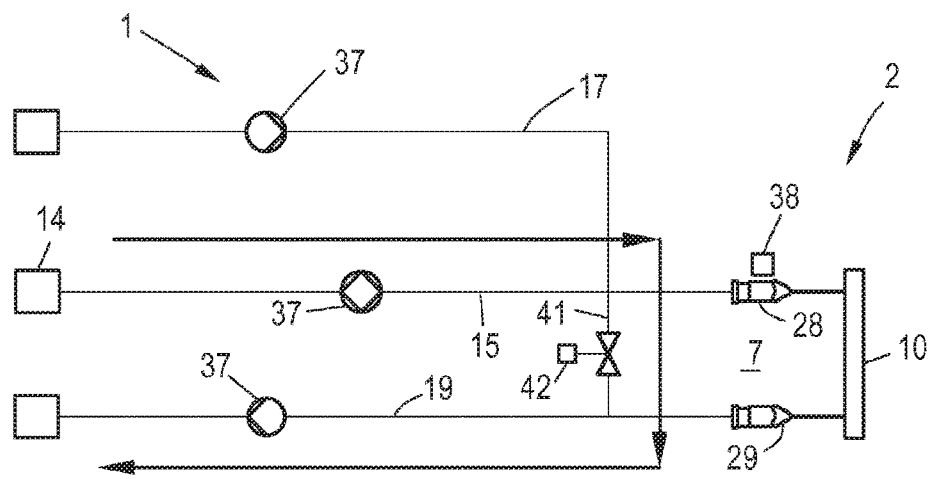

FIG. 17 shows an example of an operating mode for the realization of an emptying of the feed line 15, following the flushing of the feed line 15, and of the emptying of the withdrawal device 14 upstream of the feed line. The emptying of the feed line 15 and of the withdrawal device 14 is accomplished by the opening of the valve device 42 installed in the bypass line 41, so that flushing fluid residues can be conveyed, i.e., pumped, via the discharge line 19 out of the feed line 15 and out of the withdrawal device 14.

Figure 18:
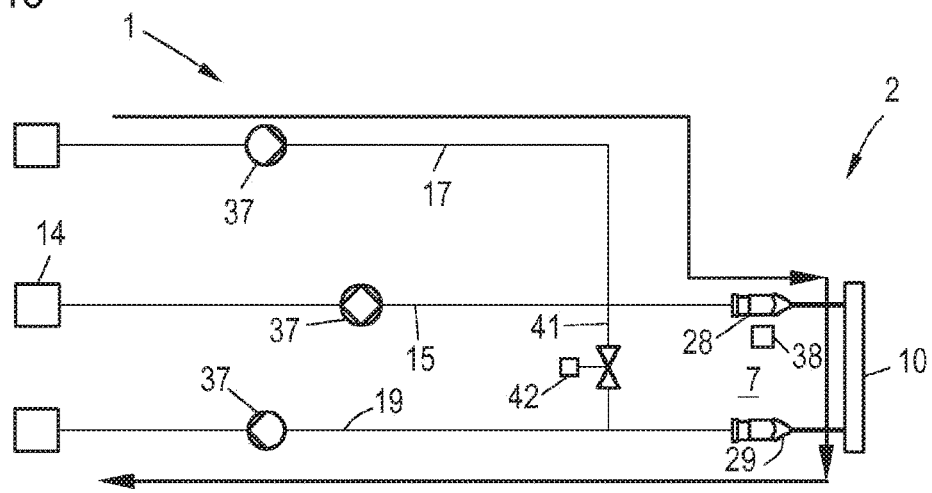

FIG. 18 shows an example of an operating mode for the realization of a flushing of the feed and discharge device 7 and of a urine test strip 10. As can be seen, flushing fluid, provided by the flush toilet flushing device 43 via the fresh water feed line 17, in particular water, is conveyed, i.e., pumped, through the feed and discharge device 7 and through the urine test strip 10, i.e., in particular through the urine test strip analysis chamber 9. The valve devices 18 and the valve device 42 installed in the bypass line 41 are switched in such a way that during this phase the flushing fluid cannot flow into the feed line 15.

Figure 19:
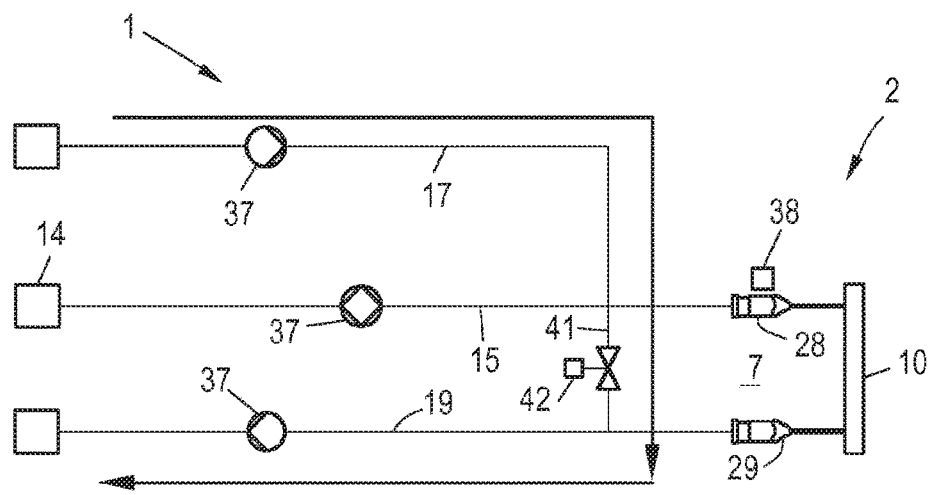

Finally, FIG. 19 shows an example of an operating mode for the realization of a flushing of the discharge line 19, which can be carried out after the flushing of the feed and discharge device 7 and of the urine test strip 10. As can be seen, flushing fluid, especially water provided by the flush toilet flushing device 43 via the fresh water feed line 17 is conveyed, i.e., pumped, through the discharge line 19. The valve devices 18 and the valve device 42 installed in the bypass line 41 are closed during this phase so that the flushing fluid cannot flow into either the feed line 15 or into the feed and discharge device 7.

The operation of the sanitary facility 1, i.e., of the apparatus 2, i.e., in particular the execution of the operating modes described with reference to FIGS. 14-19, are controlled by a central control unit (not shown).

The control unit communicates for this purpose with all of the devices of the apparatus. In the control unit there is typically at least one control program, according to which a concerted, i.e., sequentially coordinated, control of the operation of the feed and discharge device 7, of the detection device 11, and of other devices belonging to the apparatus 2 is possible. The latter include in particular appropriate pressure-determining devices 38, pump devices 37, and the valve devices 18, 42.

The detection device 11 is typically set up to communicate with at least one evaluation unit, which is set up to evaluate the detection data generated by the detection device and to acquire evaluation data describing an analysis of the urine present on the analysis zone of the urine test strip. As previously mentioned, the evaluation unit can be part of the apparatus 2 or can be an external unit. In the latter case, the apparatus 2 comprises a transmitting and/or receiving device (not shown) assigned to the detection device 11, so that corresponding detection data can be transmitted in either hard-wired or wireless fashion. The sanitary facility 1, i.e., the apparatus 2, is therefore connected by means of Bluetooth, WiFi, etc., to a local or global data network, i.e., for example, to a local intranet or to the Internet or is integrated into such a network. Correspondingly, detection data can be transmitted to appropriate evaluation units, in which, on the basis of the detection data, conclusions can be drawn concerning the chemical composition and/or the percentages of the constituents of the quantity of urine applied to the analysis zone.

The invention claimed is:

1. An apparatus for the analysis of urine, comprising:
   a urine test strip comprising an analysis chamber having at least one analysis zone, wherein at least a part of the analysis zone is surrounded by at least one encapsulating element to form at least an area of fluid-tight encapsulation;
   a feed and discharge device, which is set up to deliver a certain quantity of urine to the analysis chamber of the urine test strip and for carrying away a certain quantity of urine from the analysis chamber of the urine test strip, wherein the feed and discharge device comprises at least one movably supported feed and discharge element for delivering a certain quantity of urine to a delivery zone of the analysis chamber of the urine test strip and to carry away a certain quantity of urine from a discharge zone of the analysis chamber of the urine test strip, and at least one drive device connected to the at least one feed and discharge element and configured to move the at least one feed and discharge element toward at least one of the delivery zone and the discharge zone such that a cannula-like tip of the feed and discharge element penetrates into the at least one of the delivery zone and the discharge zone to deliver or to carry away the quantity of urine or a certain quantity of urine into or out of the urine test strip analysis chamber; and
   a detection device, which is set up to detect a change, at least in a certain area, in at least one optically detectable parameter of the at least one corresponding analysis zone of the urine test strip or of a corresponding test strip, which parameter changes in an optically detectable manner as a function of the composition of a quantity of urine contacting the analysis zone, and to generate detection data which describe at least one optically detectable parameter of the analysis zone or of a corresponding zone or which describe a change in such a parameter.

2. The apparatus according to claim 1, comprising at least one conveying device, which is set up to convey at least one urine test strip into a detection zone defined on the apparatus side, in which zone at least a certain area where there is a change in the at least one optically detectable parameter can be detected by the detection device, or to convey the test strip from the detection zone or one such zone.

3. The apparatus according to claim 2, wherein the conveying device comprises, or is configured as, at least one rotatably supported transport element with conveying sections for the conveyance of at least one urine test strip, the at least one rotatably supported transport element comprising a pimple wheel with conveying sections formed by pimples arranged a certain distance apart around the circumference for conveying at least one urine test strip, or at least one conveyor belt with conveying sections for conveying at least one urine test strip, or at least one transport roller, from which a set of several serially connected strip-like or belt-like urine test strips can be unrolled or onto which a set of several serially connected strip-like or belt-like urine test strips can be rolled.

4. The apparatus according to claim 3, wherein the conveying device comprises at least two transport rollers, wherein a set of several serially connected strip-tike or belt-like urine test strips can be unrolled from a first transport roller in such a way that at least one urine test strip to be conveyed into the detection zone can be or is moved into the detection zone and can be rolled up on to a second transport roller in such a way that the at least one urine test strip can be or is moved out of the detection zone.

5. The apparatus according to claim 1, comprising at least one separation device downstream from the detection device, which separation device is set up to separate at least one urine test strip from a set of several serially connected strip-like or belt-like urine test strips.

6. The apparatus according to claim 1, comprising at least one housing part, which is configured to hold the feed and discharge device, and the detection device.

7. The apparatus according to claim 1, comprising at least one bypass line, which connects a feed line leading to a feed element and a discharge line leading to a discharge element, wherein at least one valve device for opening and closing the bypass line is installed in the bypass line.

8. The apparatus according to claim 1, wherein the detection device is set up to communicate with at least one evaluation device, which is set up to evaluate detection data generated by the detection device and to acquire evaluation data describing an analysis of the quantity or urine present on the analysis zone of the urine test strip.

9. The apparatus according to claim 1, comprising a control unit, which is set up to control the operation of the feed and discharge device and the detection device.

10. A sanitary facility comprising a flush toilet of the wall-hung or floor-mounted type, with a base body, and with an apparatus according to claim 1.

11. The sanitary facility according to claim 10, comprising at least one withdrawal device formed or arranged in the base body, comprising at least one tubular element arranged in an opening in the base body, which tubular element is movably supported relative to a closing element between an open position and a closed position.

12. The sanitary facility according to claim 11, wherein the tubular element comprises a connection means on or in the area of the free end facing away from the base body for establishing a connection to the feed and discharge device of the apparatus or to one such device.

13. The sanitary facility according to claim 10, wherein a discharge line leading from the feed and discharge device or from one such device leads to an interior space, the boundaries of which are formed by the base body.

14. The sanitary facility according to claim 10, comprising at least one flushing device for performing a flushing operation of the flush toilet, wherein at least one fluid line of the flushing device is or can be connected to the feed line or to one such feed line leading to a feed and discharge device of the apparatus.

15. A urine test strip device, for receiving a certain quantity of urine from a feed and discharge device for analysis of the urine and having at least one parameter detectable by a detection device as a function of the composition of the urine, the urine test strip device comprising:
at least one urine test strip with an analysis chamber comprising a delivery zone for receiving the certain quantity of urine, at least one analysis zone for the analysis of the urine, and a discharge zone to carry away the urine, wherein
at least a certain part of the analysis zone is surrounded by at least one encapsulating element to form at least a certain area of fluid-tight encapsulation,
the encapsulating element comprises an upper encapsulating element section surrounding the exposed surface of the analysis zone and a lower encapsulating element section surrounding the surface of the analysis zone facing away from the exposed surface of the analysis zone, and
the lower encapsulating element section is provided with elastic properties, at least in the areas lying opposite the delivery zone and the discharge zone, so that the lower encapsulating element surrounds and seals off the part of the feed and discharge element which has perforated and penetrated into the delivery zone and the discharge zone.

16. The urine test strip device according to claim 15, wherein the analysis zone is formed between a delivery zone for delivering a certain quantity of fluid, especially a quantity of urine, to the analysis chamber and a discharge zone for carrying away a certain quantity of fluid, especially a quantity of urine, from the analysis chamber, wherein at least a certain part of the delivery zone or of the discharge zone is surrounded by the encapsulating element or by at least one additional such element to form at least a certain area of fluid-tight encapsulation.

17. The urine test strip device according to claim 16, wherein the delivery zone or the discharge zone comprises a convexity.

18. The urine test strip device according to claim 15, wherein at least a certain part of the upper encapsulating element section is made of a transparent material.

19. The urine test strip device according to claim 15, wherein a perforated area can be or is closed off with a sealing effect by the sections of material of the lower encapsulating element section surrounding this perforated area.

20. The urine test strip device according to claim 15, wherein the lower encapsulating element section is made of an elastic plastic material.

21. The urine test strip device according to claim 15, wherein the at least one urine test strip comprises several urine test strips, which are serially connected to each other in a strip-tike or belt-like fashion to form a set comprising several urine test strips.

* * * * *